United States Patent
Zhao

(10) Patent No.: US 11,072,536 B2
(45) Date of Patent: Jul. 27, 2021

(54) METHOD AND PROCESS OF PRODUCING AMMONIA FROM METHANE HYDRATE

(71) Applicant: Ji-Cheng Zhao, Dublin, OH (US)

(72) Inventor: Ji-Cheng Zhao, Dublin, OH (US)

(*) Notice: Subject to any disclaimer, the term of this patent is extended or adjusted under 35 U.S.C. 154(b) by 760 days.

(21) Appl. No.: 15/899,048

(22) Filed: Feb. 19, 2018

(65) Prior Publication Data
US 2019/0071315 A1   Mar. 7, 2019

Related U.S. Application Data

(60) Provisional application No. 62/463,107, filed on Feb. 24, 2017.

(51) Int. Cl.
| | |
|---|---|
| *C01C 1/04* | (2006.01) |
| *C07C 7/00* | (2006.01) |
| *C01B 3/48* | (2006.01) |
| *C01B 3/02* | (2006.01) |

(52) U.S. Cl.
CPC .......... *C01C 1/0405* (2013.01); *C01B 3/025* (2013.01); *C01B 3/48* (2013.01); *C07C 7/00* (2013.01); *C01B 2203/0233* (2013.01); *C01B 2203/0283* (2013.01); *C01B 2203/068* (2013.01); *C01B 2203/1241* (2013.01)

(58) Field of Classification Search
CPC .... C01B 2203/0233; C01B 2203/0283; C01B 2203/068; C01B 2203/1241; C01B 3/025; C01B 3/48; C01C 1/0405; C07C 7/00; Y02P 20/52; B01D 53/1475
See application file for complete search history.

(56) References Cited

U.S. PATENT DOCUMENTS

| | | | | |
|---|---|---|---|---|
| 8,129,316 B2 * | 3/2012 | Kvamme | ................. | C09K 8/52 507/211 |
| 2014/0120023 A1 * | 5/2014 | Singh | .................. | B01J 19/2475 423/359 |

* cited by examiner

*Primary Examiner* — Anthony J Zimmer
*Assistant Examiner* — Syed T Iqbal

(57) ABSTRACT

The present invention discloses a method and a process of producing ammonia from methane extracted from methane-hydrate at the site of methane-hydrate extraction. The method and the process comprise coupled chemical reactions. During the first reaction, carbon dioxide reacts methane-hydrate to produce carbon-dioxide-hydrate and methane: carbon dioxide+methane-hydrate⇌carbon-dioxide-hydrate+methane ($CO_2$+$CH_4$-hydrate⇌$CO_2$-hydrate+$CH_4$). The produced methane is reacted with water to produced carbon dioxide and hydrogen via the second reaction: methane+water⇌carbon dioxide+hydrogen ($CH_4$+$2H_2O$⇌$CO_2$+$4H_2$). One embodiment of the second reaction is a combination of the methane steam reforming reaction ($CH_4$+$H_2O$⇌$CO$+$3H_2$) and the water-gas shift reaction ($CO$+$H_2O$⇌$CO_2$+$H_2$), both are widely known in the art. The carbon dioxide produced in the second reaction is recycled and used for the first reaction. The hydrogen produced in the second reaction is reacted with nitrogen produced from an air separation process that is known in the art to produce ammonia via the third reaction: nitrogen+hydrogen→ammonia ($N_2$+$3H_2$→$2NH_3$). One embodiment of the third reaction is the well-known Haber-Bosch process. The current invention is related to co-locating the ammonia synthesis at the methane-hydrate extraction sites to minimize the cost of transporting both methane and carbon dioxide over long distances. The process and the associated method also have the advantage of on-site carbon sequestration. The ammonia product produced via the current invention is easily transportable in liquid form from the production sites to the end-use sites as a carbon-free liquid fuel, a fertilizer and a chemical feedstock.

7 Claims, No Drawings

US 11,072,536 B2

METHOD AND PROCESS OF PRODUCING AMMONIA FROM METHANE HYDRATE

CROSS-REFERENCE TO RELATED APPLICATION

This application claims priority under 35 U.S.C. § 119(e) to U.S. Provisional Patent Application No. 62/463,107, entitled "METHOD AND PROCESS OF PRODUCING AMMONIA FROM METHANE HYDRATE", and filed on 24 Feb. 2017, which application is hereby incorporated by reference.

GOVERNMENT INTEREST STATEMENT

This invention was made while the inventor was employed by the United States Government. The United States Government has certain rights in the invention.

FIELD OF THE INVENTION

The present invention discloses a method and a process of performing on-site conversion of methane extracted from methane-hydrate into ammonia using coupled chemical reactions. The invention is related to co-locating ammonia synthesis at the methane-hydrate extraction sites to minimize both the cost of transporting methane from the methane-hydrate extraction sites to receiving terminals for distribution and the cost of transporting carbon dioxide from sequestration sites to the methane-hydrate extraction sites. The process and the associated method also have the advantage of on-site carbon sequestration. The ammonia produced via the current invention is easily transportable in liquid form from the production sites to the receiving terminals and end-use sites as a carbon-free liquid fuel, a fertilizer and a chemical feedstock.

BACKGROUND OF THE INVENTION

Methane-hydrate is also called methane clathrate, or natural-gas-hydrate, or gas-hydrate, hydromethane, among other names. It is essentially a form of methane ($CH_4$) molecules embedded inside water cages, and it has a chemical formula of $CH_4.5.75H_2O$ or $4CH_4.23H_2O$ or other variants depending on its various crystal structures and the degree of occupancy of methane in the water cages. Methane-hydrate is widespread in continental margins and slope sediments in oceans as well as in permafrost areas. More than 90% of the methane-hydrate is in the ocean marine environment, thus cost-effective extraction of methane from methane-hydrate in continental margins and slope sediments is very significant to take advantage of this form of energy. Reservoirs of methane-hydrate can supply the worldwide energy needs for decades as described in the study performed by the United States National Academies "Realizing the Energy Potential of Methane Hydrate for the United States" (National Academies Press, 2010; ISBN: 978-0-309-14889-4; http://dx.doi.org/10.17226/12831) as well as a study performed by the United Nations Environment Programme and published as "Frozen Heat: A UNEP Global Outlook on Methane Gas Hydrates" (Edited by Y. C. Beaudoin, R. Boswell, S. R. Dallimore and W. Waite; http://wedocs.unep.org/rest/bitstreams/16659/retrieve).

There are challenges associated with extraction of methane from methane-hydrate, especially from the off-shore marine environment where most reservoirs of methane-hydrate reside. Since methane is a gas, the most efficient way of transporting it is via pipelines. However, the distance from the methane-hydrate extraction sites to the receiving terminals of natural gas pipeline stations on the continents can be very long, which can make the cost of underwater pipeline construction very high. Since the methane-hydrate extraction sites may need to be moved frequently as the local extractable resources deplete; parts of the pipelines may also need to be moved with time—adding additional cost to the methane transport.

One of the other challenges is the effectiveness of extracting methane-hydrate. The extraction has been tested using conventional hydrocarbon recovery techniques by drilling production wells to access the methane hydrate and then by heating or depressurization to release methane. Such conventional extraction methods have yet been demonstrated to be economic in large-scale methane production.

In order to accelerate the release of methane from methane hydrate, carbon dioxide ($CO_2$) has been used for the extraction (Brian Anderson, Ray Boswell, Timothy S. Collett, Helen Farrell, Satoshi Ohtsuki, Mark White, and Margarita Zyrianova: "Review of the findings of the Ignik Sikumi $CO_2$—$CH_4$ gas hydrate exchange field trial", Proceedings of the $8^{th}$ International Conference on Gas Hydrates (ICGH8-2014), Beijing, China, Jul. 28-Aug. 1, 2014). The results show that $CO_2$—$CH_4$ exchange can be accomplished in natural reservoirs although the extent is not yet known. Carbon-dioxide-hydrate ($CO_2$-hydrate) is a form of carbon dioxide molecules embedded inside water cages in a similar fashion as methane in methane-hydrate. Carbon-dioxide-hydrate is thermodynamically more stable than methane-hydrate, enabling the exchange/displacement reaction to take place as demonstrated in several studies such as (1) Z. W. Ma, P. Zhang, H. S. Bao, and S. Deng: "Review of fundamental properties of $CO_2$ hydrates and $CO_2$ capture and separation using hydration method", Renewable and Sustainable Energy Reviews, volume 53, pages 1273-1302, 2016; (2) Catherine M. R. Yonkofski, Jake A. Horner, Mark D. White: "Experimental and numerical investigation of hydrate-guest molecule exchange kinetics", Journal of Natural Gas Science and Engineering, volume 35, pages 1480-1489, 2016; and (3) Jiafei Zhao, Kun Xu, Yongchen Song, Weiguo Liu, Weihaur Lam, Yu Liu, Kaihua Xue, Yiming Zhu, Xichong Yu, and Qingping Li: "A review on research on replacement of $CH_4$ in natural gas hydrates by use of $CO_2$", Energies, volume 5, pages 399-419, 2012.

The density of carbon-dioxide-hydrate is about 1.12-1.14 $g/cm^3$, which is higher than ocean water and thus it will stay at the bottom of the ocean; therefore the $CO_2$—$CH_4$ exchange/displacement also serves as a good means for carbon sequestration.

The supply and transport of carbon dioxide to the methane-hydrate extraction sites, however, add significant cost; especially for the marine environment.

SUMMARY OF THE INVENTION

Accordingly, the above-identified shortcomings of existing processes are overcome by embodiments of the present invention. Embodiments of this invention comprise co-locating an ammonia synthesis facility/apparatus/plant with a methane-hydrate extraction operation in close proximity such that the cost of transporting both methane and carbon dioxide can be practically eliminated. Here close proximity is defined as within ten miles and one embodiment of the current invention is to integrate the ammonia synthesis apparatus on the same ocean platform of a methane-hydrate extraction operation, thus enabling coupled reactions to take place to extract methane from methane-hydrate and then convert the methane to ammonia to be used as a carbon-free fuel, a fertilizer and a chemical feedstock. Ammonia in liquid form is much more cost-effective and easier to transport than methane (natural gas) or carbon dioxide using ocean tankers over water as well as liquid-fuel trucks and pipelines on land.

The invention also enables on-site carbon dioxide sequestration/capture without transporting it over long-distances.

Further features, aspects and advantages of the present invention will be more readily apparent to those skilled in the art during the course of the following detailed description.

DETAILED DESCRIPTION OF THE INVENTION

For the purposes of promoting an understanding of the invention, the terminology used herein is for the purpose of description, not limitation. Specific reactions, methods and processes disclosed herein are meant to be used as examples. Various variants or embodiments should be considered as part of this invention.

One embodiment of the invention is to have the ammonia synthesis apparatus located on the same ocean platform as the methane-hydrate extraction. Examples of ocean platforms include those currently used for off-shore gas or oil productions that are known to those skilled in the art.

Another embodiment of the invention is to have the ammonia synthesis apparatus on a separate ocean platform but placed in close proximity to the methane-hydrate extraction platform. Here close proximity is defined as within ten miles from each other. One further embodiment of this invention is to have the two platforms tied together so pipes can be used to transfer chemicals such as carbon dioxide and methane between the platforms.

The close proximity enables the following chemical reactions to take place without long-distance transport of both methane and carbon dioxide.

In Reaction #1, carbon dioxide reacts methane-hydrate to produce carbon-dioxide-hydrate and methane: carbon dioxide+methane-hydrate⇌carbon-dioxide-hydrate+methane ($CO_2$+$CH_4$-hydrate⇌$CO_2$-hydrate+$CH_4$). Since carbon-dioxide-hydrate is more stable than methane-hydrate, Reaction #1 is thermodynamically favorable and has been experimentally demonstrated (For instance, N. Goel, "In situ methane hydrate dissociation with carbon dioxide sequestration: Current knowledge and issues." Journal of Petroleum Science and Engineering, volume 51, no. 3-4, pages 169-184, 2006). Reaction #1 is also slightly exothermic, producing a small amount of heat during the reaction.

Reaction #1 is kinetically sluggish when gaseous or liquid carbon dioxide is reacting with solid methane-hydrate (methane hydrate in solid ice). In one embodiment of the current invention, the gaseous or liquid carbon dioxide is reacting with a molten state of methane-hydrate (methane hydrate in liquid water) to accelerate the reaction rate. Such a liquid state of methane-hydrate exists according to the methane-hydrate phase diagram as shown in the publication of Jiafei Zhao, Kun Xu, Yongchen Song, Weiguo Liu, Weihaur Lam, Yu Liu, Kaihua Xue, Yiming Zhu, Xichong Yu, and Qingping Li: "A review on research on replacement of $CH_4$ in natural gas hydrates by use of $CO_2$", Energies, volume 5, pages 399-419, 2012. In one further embodiment of the current invention, the exothermic heat of Reaction #1 is employed to locally melt the solid methane-hydrate (methane-hydrate in solid ice) to help create the state of molten methane-hydrate.

The initial batch of carbon dioxide used for Reaction #1 can be provided by carbon dioxide sequestration from power plants or other sources and is transported to methane-hydrate extraction site. The initial batch of carbon dioxide can also be produced by converting methane on site using Reaction #2, whereas the initial methane is extracted from methane-hydrate using conventional processes such as heating and decompression of methane hydrate that is known in the art. Subsequent continuous carbon dioxide input for Reaction #1 will be provided by Reaction #2 on site.

The methane produced in Reaction #1 is reacted with water (steam) to produce carbon dioxide and hydrogen via Reaction #2: methane+water⇌carbon dioxide+hydrogen ($CH_4$+2 $H_2O$⇌$CO_2$+4 $H_2$). This second reaction is a combination of the methane steam reforming reaction ($CH_4$+$H_2O$⇌$CO$+3$H_2$) and the water-gas shift reaction ($CO$+$H_2O$⇌$CO_2$+$H_2$), both are widely known in the art as described in the publication Jianguo Xu and Gilbert F. Froment, "Methane steam reforming, methanation and water-gas shift: 1. Intrinsic kinetics", AIChE Journal, volume 35, no. 1, pages 88-96, 1989. The carbon dioxide produced in Reaction #2 is recycled to be used for Reaction #1; and when reaching a steady state, Reaction #1 and Reaction #2 are occurring simultaneously and feeding off of each other.

The hydrogen produced in Reaction #2 is reacted with nitrogen extracted from air via an air separation process that is known in the art to produce ammonia via Reaction #3: nitrogen+hydrogen→ammonia ($N_2$+3 $H_2$→2 $NH_3$). One embodiment of Reaction #3 is the Haber process which is also known as Haber-Bosch process that is used worldwide to produce ammonia as described by Max Appl in "Ammonia", Ullmann's Encyclopedia of Industrial Chemistry, Weinheim: Wiley-VCH, 2005.

The heat required for both Reaction #2 and Reaction #3 are produced by combustion of part of the methane produced on-site via Reaction #1. The electricity required for the operations of pumps and other necessary equipment can be generated using a gas turbine with part of the methane from Reaction #1. One embodiment of the invention is to use the oxygen separated from the air separation process (for ammonia production) as input to the gas turbine to produce high concentration of carbon dioxide that can also be captured and used as part of the input to Reaction #1. The exhaust heat generated by the gas turbines may further be used for the ammonia production and thus the gas turbine may serve the dual purpose of combined heat and power.

Another embodiment of the invention is to use wind turbines installed or floating near the combined methane hydrate extraction and ammonia synthesis site to provide electricity required for the operations.

Various embodiments of the invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. It is intended that the present invention cover all suitable modifications and variations as come within the scope of the appended claims and their equivalents.

What is claimed is:

1. A method for producing ammonia from methane-hydrate at the location of the methane-hydrate extraction, the method comprising:

providing at said location of the methane-hydrate extraction carbon dioxide to react with methane-hydrate to produce methane and carbon-dioxide-hydrate via a first reaction, wherein the first reaction is: carbon dioxide+methane-hydrate⇌carbon-dioxide-hydrate+methane ($CO_2$+$CH_4$-hydrate⇌$CO_2$-hydrate+$CH_4$);

providing methane produced from the first reaction to react with water to produce carbon dioxide and hydrogen via a second reaction, wherein the second reaction is: methane+water⇌carbon dioxide+hydrogen ($CH_4$+$2H_2O$⇌$CO_2$+$4H_2$), wherein the produced carbon dioxide is provided to the first reaction and when reaching a steady state the first reaction and the second reaction are occurring simultaneously and feeding off of each other; and providing nitrogen from an air separation process to react with the hydrogen produced from the second reaction to synthesize ammonia via a third reaction: nitrogen+hydrogen→ammonia ($N_2$+$3H_2$→$2NH_3$).

2. A method for producing ammonia from methane-hydrate at the location of the methane-hydrate extraction as cited in claim 1, wherein the first reaction takes place in molten methane-hydrate.

3. A method for producing ammonia from methane-hydrate at the location of the methane-hydrate extraction as cited in claim 1, wherein the second reaction, methane+water⇌carbon dioxide+hydrogen ($CH_4$+$2H_2O$⇌$CO_2$+$4H_2$), is a combination of a methane steam reforming reaction ($CH_4$+$H_2O$⇌$CO$+$3H_2$) and a water-gas shift reaction ($CO$+$H_2O$⇌$CO_2$+$H_2$).

4. A method for producing ammonia from methane-hydrate at the location of the methane-hydrate extraction as cited in claim 1, wherein the third reaction, nitrogen+hydrogen→ammonia ($N_2$+$3H_2$→$2NH_3$), is the widely used Haber-Bosch synthesis method.

5. A method for producing ammonia from methane hydrate at the location of the methane hydrate extraction as cited in claim 1, wherein both the processes of the second reaction and the third reaction take place on the same ocean platform.

6. A method for producing ammonia from methane hydrate at the location of the methane hydrate extraction as cited in claim 1, wherein the processes of the second reaction and the third reaction take place on separate ocean platforms which are within ten miles from one another.

7. A method for producing ammonia from methane hydrate at the location of the methane hydrate extraction as cited in claim 1, wherein the processes of the second reaction and the third reaction take place on separate ocean platforms which are linked together via pipes from one another to transport both methane and carbon dioxide among the platforms.

* * * * *